(12) United States Patent
Neighbour et al.

(10) Patent No.: US 12,383,648 B2
(45) Date of Patent: Aug. 12, 2025

(54) STERILIZATION OF FACE MASKS AND FACE MASK COMPONENTS

(71) Applicants: Aaron Neighbour, Danville, CA (US); Jessica Williams, El Dorado Hills, CA (US)

(72) Inventors: Aaron Neighbour, Danville, CA (US); Jessica Williams, El Dorado Hills, CA (US)

( * ) Notice: Subject to any disclaimer, the term of this patent is extended or adjusted under 35 U.S.C. 154(b) by 970 days.

(21) Appl. No.: 17/446,155

(22) Filed: Aug. 26, 2021

(65) Prior Publication Data

US 2022/0125979 A1 Apr. 28, 2022

Related U.S. Application Data

(60) Provisional application No. 63/045,034, filed on Jun. 26, 2020.

(51) Int. Cl.
*A61L 2/26* (2006.01)
*A61L 2/08* (2006.01)

(52) U.S. Cl.
CPC ............... *A61L 2/26* (2013.01); *A61L 2/081* (2013.01); *A61L 2/082* (2013.01); *A61L 2/087* (2013.01); *A61L 2202/181* (2013.01); *A61L 2202/24* (2013.01); *A61L 2202/26* (2013.01)

(58) Field of Classification Search
CPC . A61L 2/08; A61L 2/081; A61L 2/082; A61L 2/087; A61L 2/26; A61L 2202/181; A61L 2202/24; A61L 2202/26
See application file for complete search history.

(56) References Cited

U.S. PATENT DOCUMENTS 6,880,242 B2 * 4/2005 Van Antwerp ........ H01L 23/556
29/840

OTHER PUBLICATIONS

Deangelis et al. "Gamma radiation sterilization of N95 respirators leads to decreased respirator performance." PLoS ONE 16(4): e0248859. (Year: 2021).*

* cited by examiner

*Primary Examiner* — Timothy C Cleveland
(74) *Attorney, Agent, or Firm* — Harness, Dickey & Pierce, P.L.C.

(57) ABSTRACT

A method of disinfecting personal protective masks and mask filters, includes the step of applying sterilizing ionizing radiation to the personal protective mask while it is disposed in an electromagnetically shielded container.

20 Claims, 8 Drawing Sheets

Figure 1. Transmission of SARS-CoV-2 through viral aerosols. Image of SARS-CoV-2 courtesy of the CDC.

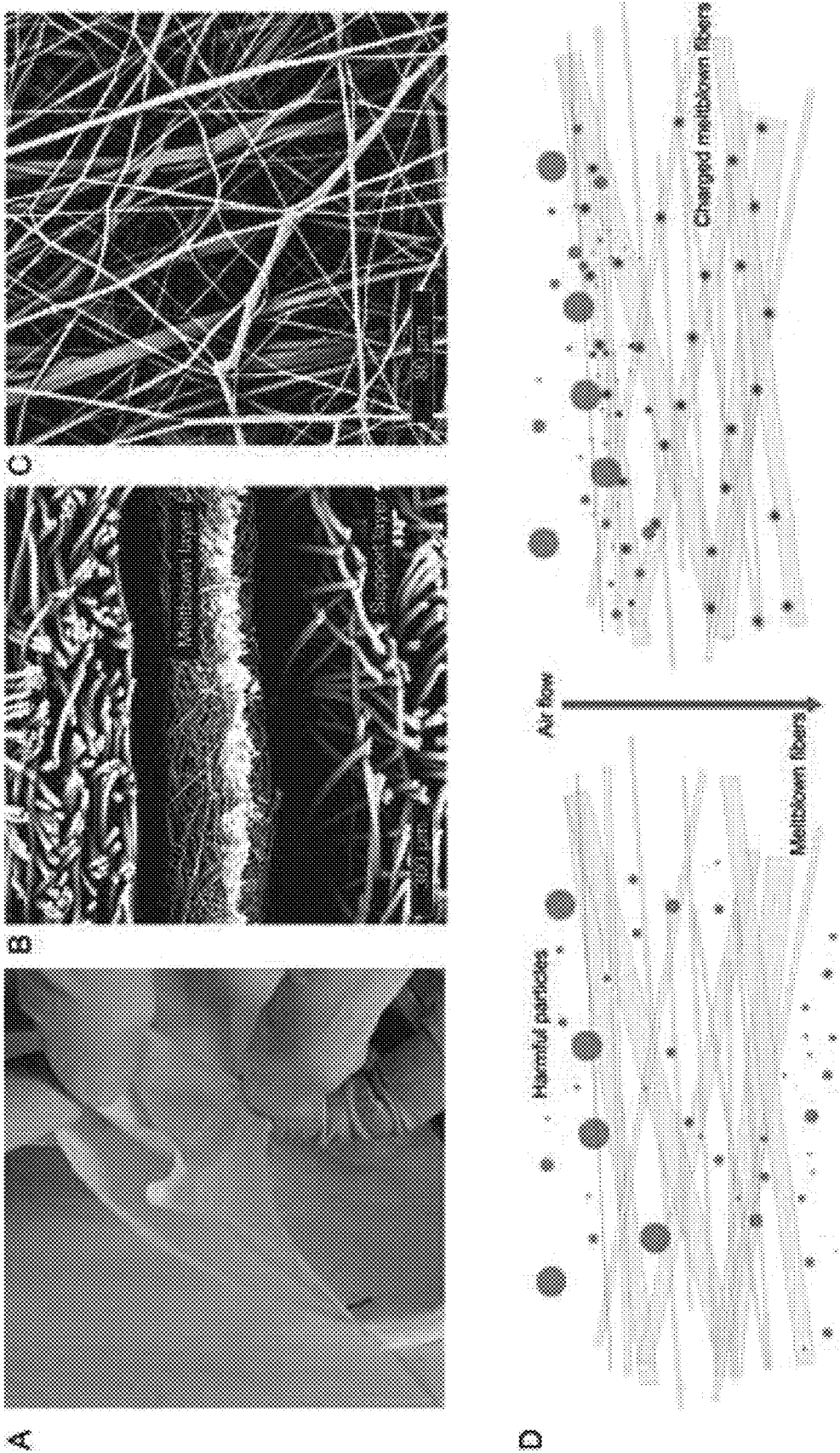
Figure 2. Meltblown fabrics in N95 FFRs.

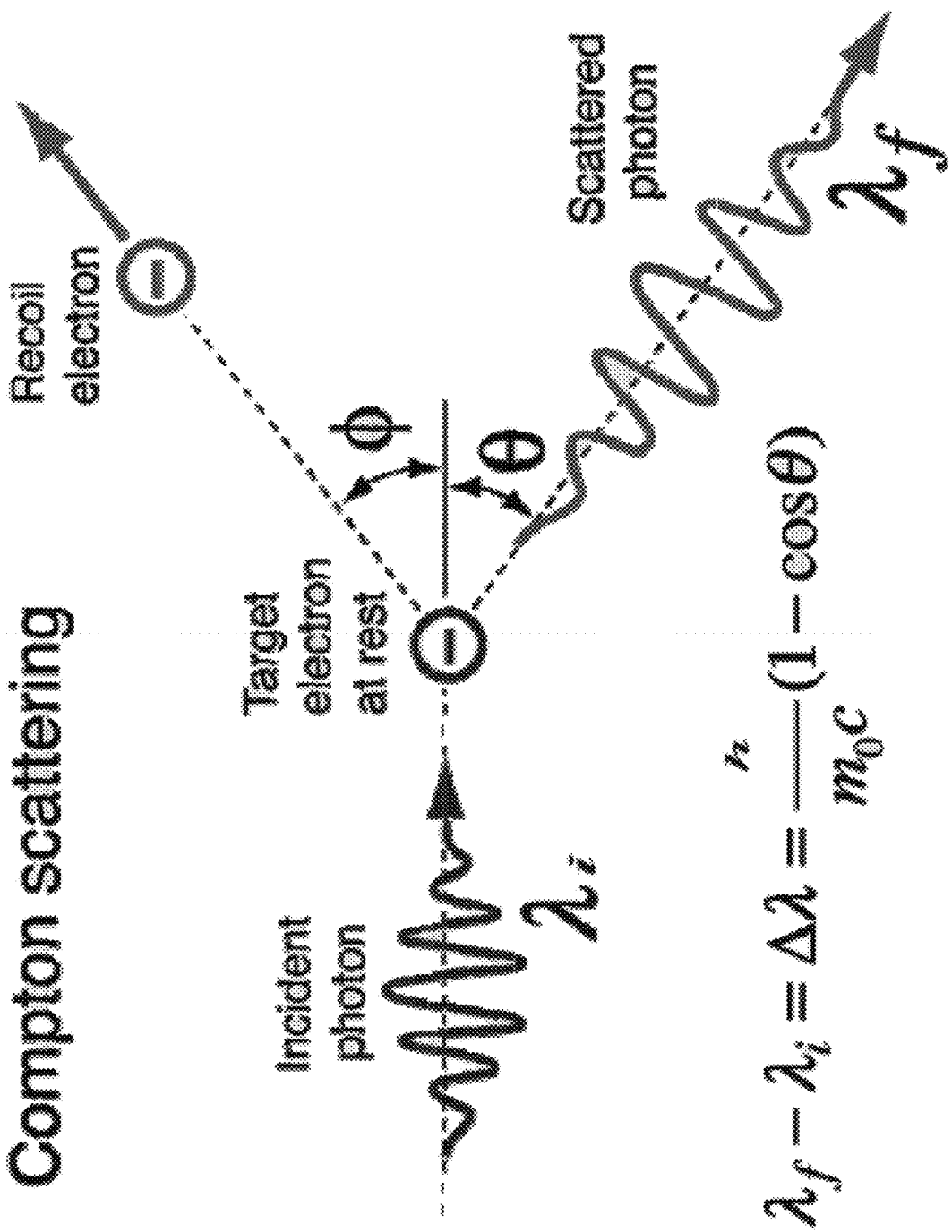
Figure 3. Compton scattering diagram.

FIGURE 4A Table of Abbreviated Mask/FFR Standards

| Mask Type | Standards | Filtration Effectiveness | | |
|---|---|---|---|---|
| Single-Use Face Mask | China: YY/T0969 | 3.0 Microns: ≥95%<br>0.1 Microns: X | | |
| Surgical Masks | China: YY/T0969 | 3.0 Microns: ≥95%<br>0.1 Microns: X | | |
| | USA: ASTM2100 | Level 1<br>3.0 Microns: ≥95%<br>0.1 Microns: ≥95% | Level 2<br>3.0 Microns: ≥98%<br>0.1 Microns: ≥98% | Level 3<br>3.0 Microns: ≥98%<br>0.1 Microns: ≥98% |
| | Europe: EN 14683 | Type I<br>3.0 Microns: ≥95%<br>0.1 Microns: X | Type II<br>3.0 Microns: ≥98%<br>0.1 Microns: X | Type III<br>3.0 Microns: ≥98%<br>0.1 Microns: X |

FIGURE 4B Table of Abbreviated Mask/FFR Standards

| Mask Type | Standards | Filtration Effectiveness | | |
|---|---|---|---|---|
| | | N95/KN95 | N99/KN99 | N100/KN100 |
| Respirator Masks | USA: NIOSH (42 CFR 84) China GB2626 | 0.3 Microns: ≥95% | 0.3 Microns: ≥99% | 0.3 Microns: ≥99.97% |
| | | FFP1 | FFP2 | FFP3 |
| | Europe: EN 14683 | 0.3 Microns: ≥80% | 0.3 Microns: ≥94% | 0.3 Microns: ≥99% |

3.0 Microns: Bacteria Filtration Efficiency Standard (BFE)

0.1 Microns: Particle Filtration Efficiency Standard (PFE)

0.3 Microns: Used to represent the most penetrating particle size (MPPS), which is the most difficult size particle to capture.

X: No requirements.

Example of a Metal-Out design for Shielding.

Metal-Out Static Shielding Bag 1500

This transparent metal-out static shielding bag is designed to provide static safe packaging for the shipment and/or storage of ESD sensitive items including outside ESD protected areas. Bags are printed with an ESD protective symbol and a lot code for traceability. Open Top and Zip Top styles are available. The bags are heat sealable.

SCS Metal-Out Static Shielding Bags 1500 are manufactured from a top coated metallized polyester and polyethylene laminate. The proprietary top coating is designed to protect the metal layer and quickly discharge any electrical field. Polyester dielectric, in concert with the metal layer, provides shielding for the bag contents from Electrostatic Discharge (ESD) and helps minimize the penetration of an electrical field.

FIG 5A

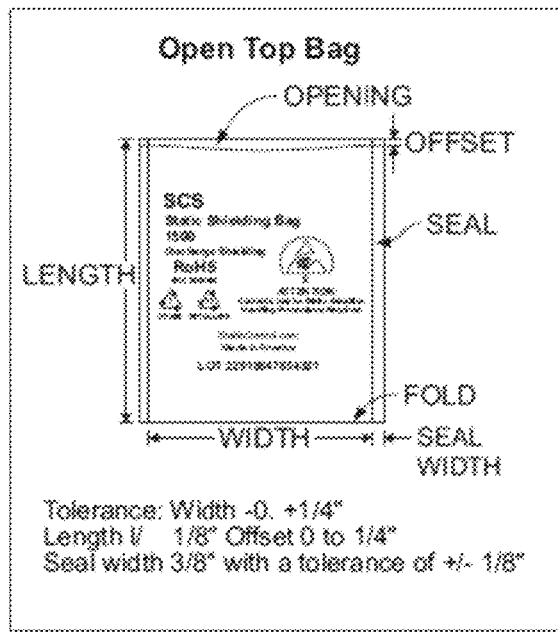

FIG 5B

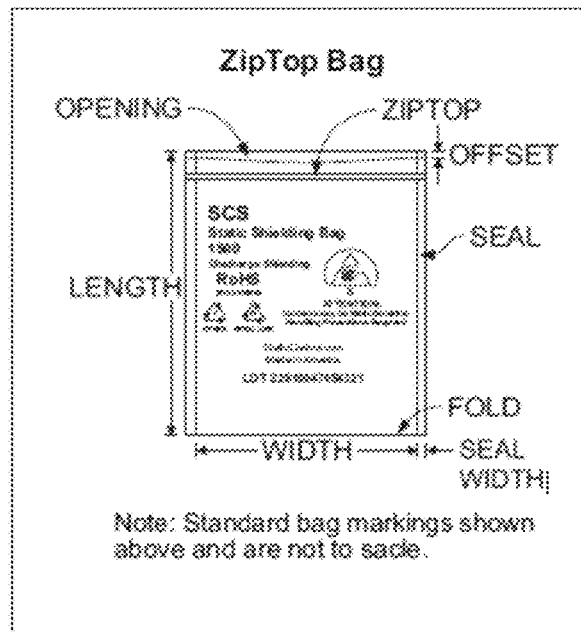

FIG 5C

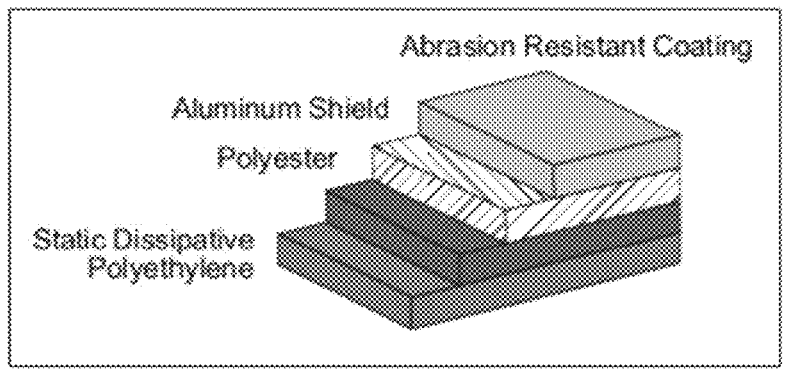

FIG 5D

Meets ANSI/ESD S20.20, Packaging Standard ANSI/ESD S541, and Static Control Bag ANSI/ESD S11.4 Level 3

| Physical | Typical Value | Testing Method |
|---|---|---|
| Puncture Resistance | 10 lbs, 44 N | MIL-STD-3010 Method 2065 |
| Seal Strength | 14 lbs, 62 N | ASTM D882 |
| Thickness | 3 mils, .0762 mm +/-10% | MIL-STD-3010 Test Method 1003 Method B |
| Marking Adhesion | Pass | IPC-TM-650 2.4.1 |
| Transparency | 40% | Tobias |
| Electrical | Typical Value | Testing Method |
| Discharge Shielding | <10 nJ | ANSI/ESD STM11.31 |
| Surface Resistance - Interior | $1 \times 10^4$ to $< 1 \times 10^{11}$ ohms | ANSI/ESD STM11.11 |
| Surface Resistance - Exterior | $1 \times 10^4$ to $< 1 \times 10^6$ ohms | ANSI/ESD STM11.11 |
| Charge Retention | <100 volts | 1410.515 |
| Cleanliness | Typical Value | Testing Method |
| Silicone | Not Detected | ASTM-E168 (FTIR) |
| Heat Sealing Conditions | Typical Value | |
| Temperature | 300°F - 375°F, 149°C - 190°C | |
| Time | 0.5 - 3.5 seconds | |
| Pressure | 30 - 70 PSI, 206 - 482 KPa | |

Bag is free of amines, N-octanoic acid, silicones and heavy metals.

RoHS, REACH, and Conflict Minerals Statement
See the Desco Industries RoHS, REACH and Conflict Minerals Statement:
DescoIndustries.com/ROHS3.aspx See the SCS Limited Warranty:
StaticControl.DescoIndustries.com/Limited-Warranty.aspx

This product is intended for commercial use only.
Specifications and procedures subject to change without notice.

Made in the
United States of America

1500 SERIES METAL-OUT STATIC SHIELDING BAG

FIG 5E

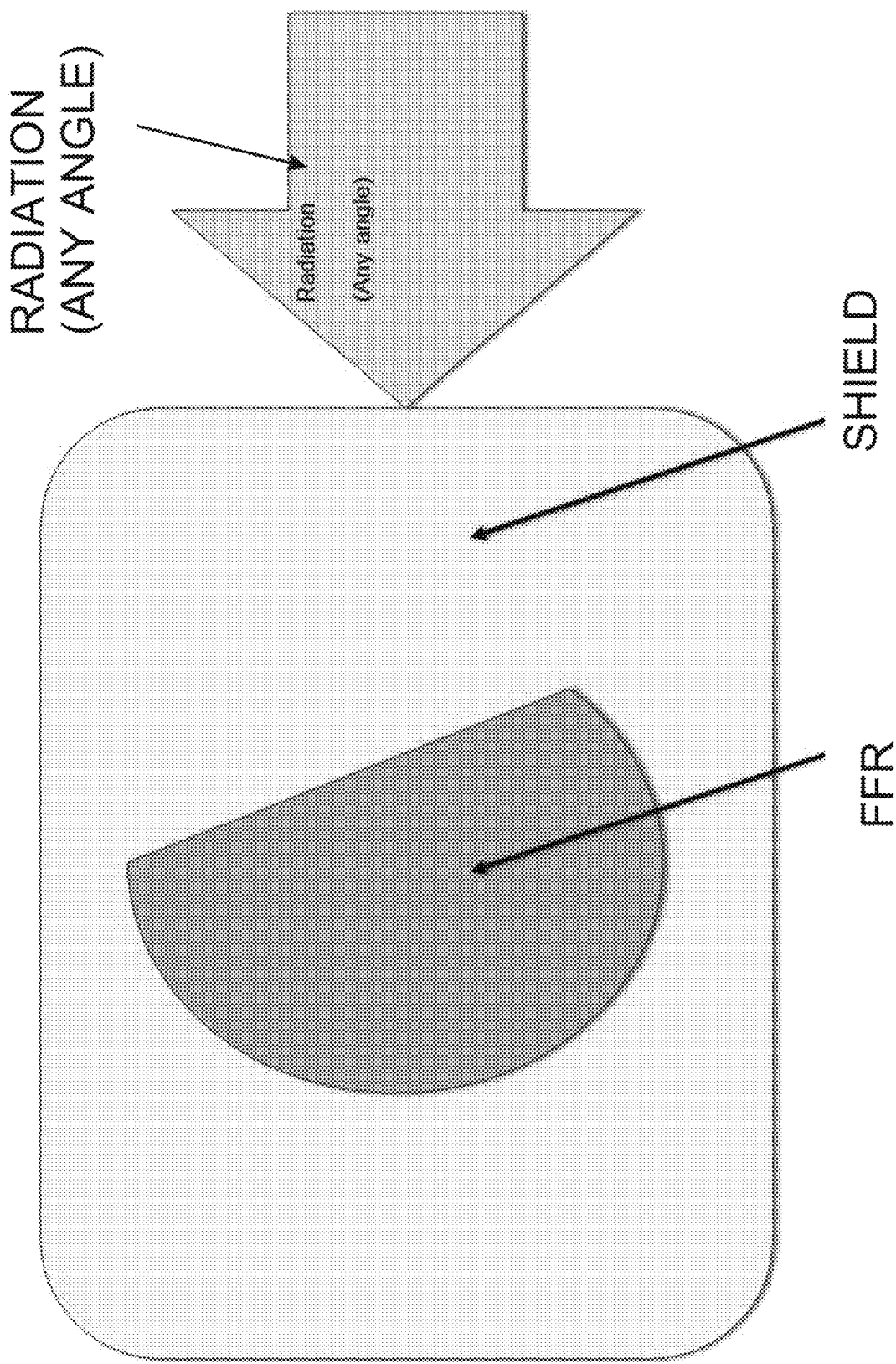
Figure 6. Diagram of setup.

STERILIZATION OF FACE MASKS AND FACE MASK COMPONENTS

FIELD

The present disclosure relates to the sterilization of face masks and face mask components, and in particular to the sterilization of N95 and similar filtering facepiece respirators (FFR).

RELATED ART

N95 rated FFR's have a nonwoven fabric filtration media of polypropylene (PP) nanofibers that are imbued with an electrostatic trait upon manufacture, usually via a meltblown process. The mechanical filtration (physical porosity of approximately 1.0-micron) of this semipermeable PP media provides some protection to the wearer; however, the NIOSH standard for N95 requires, among other criteria, that the FFR allow <5.0% of a 0.3-micron NaCl vapor to pass through the media under controlled and specified conditions. This additional filtration, above what the physical porosity can provide, is generated by the media's electrostatic properties of the constituent PP fibers.

Lower frequency forms of ionizing radiation, such as UV-C and other ultraviolet wavelengths, have been shown to partially sanitize/sterilize FFR's and have received Emergency Use Authorization by the US FDA during the COVID-19 crisis. However, UV-C photons can only disinfect surfaces (surface decontamination) that are directly exposed to said rays. PP filters are inherently cavernous places on the microscopic scale, with millions of shadowed pathways wherein viral bioburden can readily survive UV irradiation processes. Therefore, it is desirable to utilize deep penetrating, high-confidence irradiation methods of sterilization for reusing FFR's.

In an attempt to combat the shortage of FFR's, many organizations began research into using powerful irradiation methods to sterilize FFR's for reuse by frontline workers in the pandemic—including the possibility of using electron beam irradiation (E-beam)—to deliver a sterilizing dose to FFR's (like the N95 class in the United States). While such experimentally treated FFR's appeared to be mechanically intact after treatment—including the straps, nose clip, and face-seal coating—NIOSH NaCl testing revealed that the filtration efficiency of the FFR's had been reduced to an approximate range of 45%-65%. The conclusion of these organizations was that ionizing irradiation (E-beam, X-ray, and gamma) could not be used in a traditional way (exposing the FFR's in standard packaging, polypropylene plastic resin bags, or no packaging), as such methods significantly adversely affected the electrostatic properties of PP, lowering the filtration efficiency beyond acceptable limits.

Even if no morphological and very few chemical changes have been observed in the nonwoven melt-blow PP material, FFP2 filtration performance in submicronic range is seriously affected by radiation processing, whatever the dose (beyond 5 kGy) and the irradiation conditions are. The inventors believe that this effect may be linked with the electrostatic filtration provided by the electric charge (electret) to the melt-blown material used in these types of masks. Thus it appears that the decontamination radiation processing of FFPs (N95 or equivalent respiratory protection masks) should be avoided to preserve the submicron filtration efficiency of such masks. One study reports that "Gamma and E-beam irradiation, under vacuum or in air, with or without thermal annealing after irradiation, cannot be recommended for treatment for re-using such masks with the present technology." (*International Atomic Energy Agency Technical Report, STERILIZATION AND REPROCESSING OF PERSONAL PROTECTIVE EQUIPMENT (PPE), INCLUDING RESPIRATORY MASKS, BY IONIZING RADIATION.* 2020), incorporated herein by reference.

There is a need for a reliable sterilization method for stretching both existing and newly manufactured mask and respirator supplies during the COVID-19 pandemic. Shortages of suitable respirators and other mask-type PPE became its own crisis within a crisis. The United States Government has spent hundreds of millions of dollars to procure and service vapor-phase hydrogen peroxide decontamination systems for the explicit purpose of stretching supplies (reuse) of masks and respirators through surface-sanitation.

BRIEF DESCRIPTION OF THE DRAWINGS

The detailed description of some embodiments of the invention is made below with reference to the accompanying figures, wherein like numerals represent corresponding parts of the figures.

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 shows an exemplary transmission of SARS-CoV-2 through viral aerosols;

FIG. 2 shown meltblown fabrics in N95 FFRs.

FIG. 3 shows a Compton scattering diagram.

FIGS. 4A-B shows a table of abbreviated mask/FFR standards.

FIGS. 5A-5E show an example of a metal-out design for shielding.

FIG. 6 shows an exemplary diagram of the invention setup according to an embodiment of the present invention.

DETAILED DESCRIPTION

While preferred embodiments of the present disclosure are shown and described herein, it will be apparent to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

Stanford University (USA) researched and published a paper with the American Chemical Society on the topic of FFR decontamination to combat COVID-19. In it, the requirements of an effective FFR are discussed and diagrammed. The SARS-CoV-2 virus is shown to be 0.150-micron (ranges as small as 0.060-micron) in diameter (See FIG. 1) but is likely not to be an airborne transmitter in and of itself; rather, the smallest transport medium used by the live viruses to achieve successful human-to-human transmission is likely to be aerosols. Viral aerosols are sited to be between 1 and 5 microns (approximately) in diameter.

FIG. 1 shows meltblown fabrics in N95 FFRs. Referring to FIG. 2A Peeling apart a typical N95 FFR reveals multiple layers of nonwoven materials. In FIG. 2B scanning electron microscope (SEM) cross-section image reveals the middle meltblown layer has thinner fibers with thickness around 300 µm. In FIG. 2C, SEM image of meltblown fibers reveals a complicated randomly oriented network of fibers, with diameters in the range of ~1-10 µm. FIG. 2D, is a schematic illustration of meltblown fibers without (left) and with (right) electret charging. In the left figure, smaller particles are able to pass through to the user, but particles are electrostatically captured in the case of an electret (right).

FIG. 2D, is a diagrammatic depiction of the FFR's PP layers with and without an effective electrostatic charge. While the literature demonstrates that sterilizing doses from E-beam, X-ray, and Gamma sources do not mechanically damage the PP in a compromising way.

It is believed that the electrostatic charge of meltblown fibers that provides the 94-95% filtration efficiency of the FFR; these fields attract certain fine particles into the nanofibers where they impact and stick to said fibers. Without being held to the exact phenomenon or phenomena that is/are active at the level of the atoms in the nanofibers, the inventors hypothesize a potential hypothesis is as follows: Due to some combination of primary and secondary radiation (including Compton scattering, as shown in FIG. 3) that is created during the irradiation process, the vital, operative electrostatic property of the PP meltblown layer is somehow weakened as electrons are liberated from the material and removed from the system by high-energy, ionizing photons. When a sufficiently energetic photon or particle (either directly emitted from a gamma source, created via Bremsstrahlung effect, pair production, etc.) interacts with an electron in an atom, it can detach that electron from said atom. These free electrons can be absorbed by other matter and if that "other matter" is not neighboring PP fibers (by way of example), then the electrostatic properties of the source material (atoms) can be altered.

Embodiments of the present invention aim to preserve the electrostatic properties of filtration materials such meltblown PP to maintain the majority of a FFP's filtration efficiency. Specific to the COVID-19 crisis, which itself was a primary cause of the N95 shortage in the United States, the purpose of FFR irradiation is for effective sterilization and reuse of the equipment so that it may prevent wearers from contracting SARS-CoV-2. FIG. 1 shows the size of the virus to be well below the 0.3-micron testing limit (considered to be a highly penetrative particle size) of the N95 FFR (or its rough equivalents from other national standards); however, research strongly indicates that the virus is not airborne on its own (at least not in a way that allows it to effectively survive the journey). Therefore, it is the aerosolized, liquid transport medium that must be blocked by FFR's, which is probabilistically the smallest human-to-human transmission source of the virus through the air. Given their size of approximately 1-10 microns, these droplets can be satisfactorily, mechanically filtered by N95 (95%), FFP2 (94%), P2 (94%), etc. standard FFR's. On the opposite end, particles smaller than 0.3-micron (like the virus itself) are more predictably defeated by such FFR's because of Brownian motion.

The influenza virus and SARS-CoV-2 share a very similar size (with the standard size range of SARS-CoV-2 being both smaller than the min. and larger than the max. range for Influenza). Research into the effectiveness of FFR's versus medical masks has been rigorously conducted. The European Center of Diseases Control (ECDC) has stated that healthcare workers in contact with a suspected or confirmed COVID-19 case should wear a medical mask or, if available an FFP2 respirator [roughly N95 equivalent]. Most of the evidence about the use of PPE in viral infections is based on Influenza models. Despite the known similarities in terms of transmission, they should be considered with caution in the context of SARS-CoV-2 infections. A recent systematic review and meta-analysis evaluated the effectiveness of N95 respirators versus medical masks [roughly ASTM F2100 equivalent] for the prevention of influenza. It included six randomized clinical trials for a total of 9171 participants. No significant differences were found between the use of N95 respirators and medical masks for the outcomes of laboratory confirmed respiratory viral infections (RR=0.89, 95% CI0.70-1.11), laboratory-confirmed influenza (RR=1.09, 95% CI0.92-1.28), laboratory-confirmed respiratory infection (RR=0.74, 95% CI0.42-1.29), or influenza like illness (RR=0.61. 95%, CI0.33-1.14). One of the trials included was actually done in a household setting. The authors concluded suggesting that N95 respirators should not be recommended for the general public and healthcare workers performing low-risk procedures.

Specific evidence regarding SARS-CoV-2 is ongoing. A randomized multicenter controlled trial (NCT04296643) in Canada is underway to compare the use of either medical masks or N95 respirators in 576 nurses involved in the care of patients with COVID-19. The primary outcome is laboratory confirmed COVID-19 among the participants." (Ippolito M, et al. Pulmonol.2020.https://doi.org/10.1016/j.pulmoe.2020.04.009) citing (Y. Long, T. Hu, L. Liu, R. Chen, Q. Guo, L. Yang, et al., Effectiveness of N95 respirators versus surgical masks against influenza: A systematic review and meta-analysis, J Evid Based Med. (2020). https://doi.org/10.1111/jebm.12381)

The conclusion from this data is that an N95/FFP2 FFR and ASTM F2100 analogous medical masks can adequately protect wearers from contracting infectious respiratory diseases, like influenza and the aerosols that carry such viral load. From the above-cited research, FFR's of lesser filtration efficiency than N95/FFP2 can be reasonably assumed to be effective at protecting wearers from COVID-19; the Canadian trial study that can directly substantiate this claim is still ongoing. By extension, the FFP1 standards (80% filtration efficiency of 0.3-micron NaCl) could also be used effectively, as this class of respirators exceeds the filtration requirements of medical masks. See FIG. 4 for reference.

The inventors conducted preliminary dose mapping studies to irradiate a variety of FFR sample types (each type consisted a statistically significant quantity of FFR's for testing purposes and result analyses, per NIOSH standards for NaCl testing) for submission to a NIOSH certified laboratory for filtration efficiency analysis. The filtration efficiency results ranged between the mid-40's to mid-60's across the entire set of all samples, which themselves were dosed across a wide range. Some sample sets were dosed above 100 kGy. The results effectively matched published reports.

The inventors discovered an interesting correlation between their internal data and the published research data; in particular, the published work by the French contributors to the TAEA report, incorporated herein by reference, "Even if no morphological and very few chemical changes have been observed in the filtering PP material, FFP2 filtration performance in submicronic range is seriously affected by radiation processing, whatever the dose and the irradiation conditions are.

The inventors developed a novel process that incorporated a Faraday cage effect around the FFR's (either one or multiple FFR's may be present inside of a cage) using electrostatic discharge shielding material (hereby called "shielding," "static shield," "static shielding," or "shield(s)"). Conductive antistatic containers or bags are manufactured with a metallic (conductive) layer of aluminum (or other suitable metal) and/or a dielectric layer of plastic that is covered in a static dissipative coating (see FIG. 5 for reference only).

Through experimentation, the inventors have observed a positive correlation between filtration efficiency of FFR's (owing to preserved electrostatic fields) and the presence of shielding material, including multiple shielding layers, with which the FFR's are surrounded. Any use of such shielding material, metal, or metallized composites including "Metal-In" or "Metal-Out" construction (relevant to bag construction and such form factors) does not appear to materially affect the efficacy of the process. Testing has also indicated that metal foil alone, at different thicknesses, also resulted in desirable outcomes for irradiated FFR's, with filtration efficiencies ranging from the mid-80's to mid-90's. Similarly, use of standard-pressure, high-pressure, or low-pressure (near vacuum) air, or any other unreactive gas, inside a sealed, air-tight shielding membrane(s) that surrounds either a single FFR or multiple FFR's also does not appear to materially affect the efficacy of the process. Likewise, dosing, including but not limited to time of exposure, incident angle of the radiation to the target geometry, carrier system employed, power of radiation source, or energy of radiation source at or above 1.0 MeV, also does not appear to affect the efficacy of the process, provided sufficient dosing is delivered to destroy the pathogens that are present. Finally, the mode of dosing, whether single-exposure or fractionated dosing does not appear to affect the efficacy of the process, provided that the cumulative dose is sufficient to destroy the pathogens that are present. Generally, according to a preferred embodiment of the invention, a method of disinfecting personal protective masks and mask filters comprises applying sterilizing ionizing radiation to the personal protective mask or mask filter while it is disposed in an electromagnetically shielded container. This sterilizing ionizing radiation is preferably at least one of e-beam radiation, x-ray radiation, and/or gamma radiation.

In one embodiment the electromagnetically shielded container preferably comprises a metal (pure metal or metal alloy) container. The container is preferably a metal foil, such as an aluminum foil. The foil can be continuous, or it can be in the form of a web or mesh. The foil is preferably between about 10 Å and about 200 μm (the thickness of a very thick foil). More preferably the thickness of the foil is between about 10 Å and about 85 μm (the thickness of a very heavy duty foil). Still more preferably the thickness of the foil is between about 10 Å and about 25 μm (the thickness of heavy duty foil), and still more preferably between 10 Å and about 10 μm (the thickness of conventional aluminum foil).

In another embodiment, the container can be more rigid, metal plates, preferably less than about 3 cm, and more preferably less than about 1 mm, and most preferably less than about 500 μm, A wide range of thicknesses can be used provided sufficient sterilizing radiation can penetrate the metal to sterilize the masks and mask components contained therein. The plates can be continuous, or the can be perforated or fenestrated.

In still another embodiment, the electromagnetically shielded container preferably comprises at least one polymer bag having a conductive metallic layer. The polymer bag preferably comprises a layer of polyester with the conductive metal layer on at least one side. Of course more than one layer of polyester and/or more than one layer of conductive metal can be provided to form a sandwich configuration. The polymer bag preferably further comprises a layer of static dissipative material on the opposite side of the polyester layer from the conductive metal layer, or otherwise electrically isolated form the conductive metal layer. A protective layer is preferably provided over the conductive metal layer.

The conductive metal layer is preferably comprised of aluminum, but it could be some other suitable metal or metal alloy including metallic tin, copper, or silver, or their alloys. The metal layer is preferably on the order of about 10 Å and about 25 Å. One example of a suitable container is the 1300 Series Static Shielding Bag, available from Desco Industries, Inc, Sanford, N.C. This shielding bag comprises a polyester layer with a statistic dissipative coating on one side, and an aluminum shield layer on the other side, and a static dissipative polyethylene layer overlying the aluminum shield layer. Another example of a suitable container is the Statshield® bag available from Vermason Ltd., Herts, UK. This shielding bag comprises an aluminum shielding layer 10 Å to 25 Å thick, with an outer static dissipative polyester layer 0.5 mil thick, and a static dissipative inner polyethylene layer 2.5 mil thick.

The metal layer in these containers is preferably imperforate, but it could be in the form of a grid or web or mesh.

The dose of ionizing radiation need only be sufficient to kill the pathogens, without significant degradation of the mask materials. Doses between about 1 kGy and about 1,000 kGy, and more preferably between about 1 kGy and about 140 kGy, and most preferably between about 1 kGy and 40 kGy are believed to be sufficient. The ionizing radiation can be e-beam radiation, X-ray radiation, and/or gamma radiation.

The inventors have found that by irradiating masks and mask components in metal or metalized containers such as the metalized polyester bags described above a sufficient dose of ionizing radiation can be applied without substantially degrading the desirable electrostatic properties of the polymers comprising the mask filter. Each mask or mask component can be placed in its own bag, or multiple masks or mask components can be placed in the same bag. These bags can be nested one inside the other, if desired. The bags can be sealed or left unsealed during the process. It is believed that the metal or metalized containers act as a Faraday cage, protecting the electrostatic properties of the mask and mask components as they are subjected to ionizing radiation.

All references throughout this application, for example patent documents—including issued or granted patents or equivalents, patent application publications, and non-patent literature documents or other source material—are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

As used herein, the singular forms "a," "an," and "the" include plural references unless the context clearly dictates otherwise. Any reference to "or" herein is intended to encompass "and/or" unless otherwise stated.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Table 1 below shows the effect of various levels of shielding and various levels of radiation on the filtration efficiency of masks and mask parts.

| Test Series # | Description of Container with N95 FFR Inside | Approx. Min. Dose kGy | Filtration Efficiency % |
|---|---|---|---|
| 3 | Control FFR (no irradiation processing, no container) | 0 | 98.70 |
| 3 | Control FFR (no irradiation processing, no container) | 0 | 97.32 |
| 3 | Control FFR (no irradiation processing, no container) | 0 | 98.76 |
| 3 | Control FFR (no irradiation processing, no container) | 0 | 97.88 |
| 3 | Control FFR (no irradiation processing, no container) | 0 | 97.84 |
| 3 | Triple Nested Static Shield Bags | 25 | 92.16 |
| 3 | Triple Nested Static Shield Bags | 25 | 93.03 |
| 3 | Triple Nested Static Shield Bags | 25 | 93.02 |
| 3 | Quadruple Nested Static Shield Bags | 25 | 85.24 |
| 3 | Quadruple Nested Static Shield Bags | 25 | 85.42 |
| 3 | Quadruple Nested Static Shield Bags | 25 | 85.10 |
| 3 | Single Moisture Barrier (ESD) Bag | 25 | 75.82 |
| 3 | Single Moisture Barrier (ESD) Bag | 25 | 90.35 |
| 3 | Single Moisture Barrier (ESD) Bag | 25 | 96.37 |
| 3 | Double Nested Moisture Barrier (ESD) Bags | 25 | 89.54 |
| 3 | Double Nested Moisture Barrier (ESD) Bags | 25 | 89.43 |
| 3 | Double Nested Moisture Barrier (ESD) Bags | 25 | 87.54 |
| 3 | Triple Nested Moisture Barrier (ESD) Bag | 25 | 86.40 |
| 3 | Triple Nested Moisture Barrier (ESD) Bag | 25 | 89.84 |
| 3 | Triple Nested Moisture Barrier (ESD) Bag | 25 | 91.84 |
| 3 | Single Moisture Barrier (ESD) Bag nested with Double Nested Static Shield Bag | 25 | 86.16 |
| 3 | Single Moisture Barrier (ESD) Bag nested with Double Nested Static Shield Bag | 25 | 84.02 |
| 3 | Single Moisture Barrier (ESD) Bag nested with Double Nested Static Shield Bag | 25 | 78.94 |
| 3 | Double Moisture Barrier (ESD) Bags nested with Single Static Shield Bag | 25 | 81.48 |
| 3 | Double Moisture Barrier (ESD) Bags nested with Single Static Shield Bag | 25 | 76.61 |
| 3 | Double Moisture Barrier (ESD) Bags nested with Single Static Shield Bag | 25 | 89.86 |
| 3 | Double Moisture Barrier (ESD) Bags nested with Double Nested Static Shield Bags | 25 | 89.99 |
| 3 | Double Moisture Barrier (ESD) Bags nested with Double Nested Static Shield Bags | 25 | 89.81 |
| 3 | Double Moisture Barrier (ESD) Bags nested with Double Nested Static Shield Bags | 25 | 91.00 |
| 3 | Triple Nested Moisture Barrier (ESD) Bags nested with Single Static Shield Bag | 25 | 78.50 |
| 3 | Triple Nested Moisture Barrier (ESD) Bags nested with Single Static Shield Bag | 25 | 78.54 |
| 3 | Triple Nested Moisture Barrier (ESD) Bags nested with Single Static Shield Bag | 25 | 77.98 |
| 3 | Triple Nested Moisture Barrier (ESD) Bags nested with Double Nested Static Shield Bags | 25 | 82.54 |
| 3 | Triple Nested Moisture Barrier (ESD) Bags nested with Double Nested Static Shield Bags | 25 | 82.45 |
| 3 | Triple Nested Moisture Barrier (ESD) Bags nested with Double Nested Static Shield Bags | 25 | 83.48 |
| 4 | Double Nested Static Shield Bags and 25 Micron Aluminum Foil | 25 | 86.84 |
| 4 | Double Nested Static Shield Bags and 25 Micron Aluminum Foil | 25 | 91.83 |
| 4 | Double Nested Static Shield Bags and 25 Micron Aluminum Foil | 25 | 81.92 |
| 4 | Double Nested Static Shield Bags and 80 Micron Aluminum Foil | 25 | 87.14 |
| 4 | Double Nested Static Shield Bags + 80 Micron Aluminum Foil | 25 | 89.68 |
| 4 | Double Nested Static Shield Bags + 80 Micron Aluminum Foil | 25 | 93.88 |
| 4 | Triple Nested Static Shield Bags and 25 Micron Aluminum Foil | 25 | 89.36 |
| 4 | Triple Nested Static Shield Bags and 25 Micron Aluminum Foil | 25 | 87.69 |
| 4 | Triple Nested Static Shield Bags and 25 Micron Aluminum Foil | 25 | 82.42 |
| 4 | Triple Nested Static Shield Bags and 80 Micron Aluminum Foil | 25 | 83.03 |
| 4 | Triple Nested Static Shield Bags and 80 Micron Aluminum Foil | 25 | 85.85 |
| 4 | Triple Nested Static Shield Bags and 80 Micron Aluminum Foil | 25 | 79.39 |
| 4 | Single Moisture Barrier (ESD) Bag and 25 Micron Aluminum Foil | 25 | 84.91 |
| 4 | Single Moisture Barrier (ESD) Bag and 25 Micron Aluminum Foil | 25 | 88.90 |
| 4 | Single Moisture Barrier (ESD) Bag and 25 Micron Aluminum Foil | 25 | 94.06 |
| 4 | Single Moisture Barrier (ESD) Bag and 80 Micron Aluminum Foil | 25 | 86.39 |
| 4 | Single Moisture Barrier (ESD) Bag and 80 Micron Aluminum Foil | 25 | 92.39 |
| 4 | Single Moisture Barrier (ESD) Bag and 80 Micron Aluminum Foil | 25 | 89.74 |
| 4 | Single Moisture Barrier (ESD) Bag | 25 | 90.35 |
| 4 | Single Moisture Barrier (ESD) Bag | 25 | 87.02 |
| 4 | Single Moisture Barrier (ESD) Bag | 25 | 89.10 |
| 4 | 25 Micron Aluminum Foil | 25 | 89.96 |
| 4 | 25 Micron Aluminum Foil | 25 | 85.40 |
| 4 | 25 Micron Aluminum Foil | 25 | 92.80 |
| 4 | 80 Micron Aluminum Foil | 25 | 87.90 |
| 4 | 80 Micron Aluminum Foil | 25 | 95.10 |
| 4 | 80 Micron Aluminum Foil | 25 | 89.75 |
| 5 | Triple Nested Static Shield Bags | 40 | 92.92 |
| 5 | Triple Nested Static Shield Bags | 40 | 93.21 |
| 5 | Triple Nested Static Shield Bags | 40 | 85.29 |
| 5 | Triple Nested Static Shield Bags | 40 | 86.42 |
| 5 | Triple Nested Static Shield Bags | 40 | 92.82 |
| 5 | Triple Nested Static Shield Bags | 40 | 94.51 |
| 5 | Triple Nested Static Shield Bags | 40 | 88.20 |
| 5 | Triple Nested Static Shield Bags | 40 | 92.46 |
| 5 | Triple Nested Static Shield Bags | 40 | 90.65 |
| 5 | Triple Nested Static Shield Bags | 40 | 95.89 |
| 5 | Triple Nested Static Shield Bags | 40 | 93.72 |
| 5 | Triple Nested Static Shield Bags | 40 | 92.01 |
| 5 | Triple Nested Static Shield Bags | 40 | 91.91 |

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method of disinfecting personal protective masks and mask filters, comprising a step of applying sterilizing ionizing radiation externally to an electromagnetically shielded container in which at least one personal protective mask is disposed.

2. The method according to claim 1, wherein the ionizing radiation is at least one of e-beam radiation, x-ray radiation, and/or gamma radiation.

3. The method according to claim 2, wherein the electromagnetically shielded container comprises a conductive metallic layer.

4. The method according to claim 2, wherein the electromagnetically shielded container comprises a polymer bag wherein the polymer bag further comprises a conductive metallic layer.

5. The method according to claim 4, wherein the polymer bag comprises a layer of polyester with the conductive metallic layer on at least one side.

6. The method according to claim 5, wherein the polymer bag further comprises a layer of a static dissipative material on the opposite side of the polyester layer from the conductive metallic layer.

7. The method according to claim 6, wherein the polymer bag further comprises a protective layer over the conductive metallic layer.

8. The method according to claim 3, wherein the conductive metallic layer comprises aluminum.

9. The method according to claim 8, wherein the conductive metallic layer is continuous.

10. The method according to claim 8, wherein the conductive metallic layer comprises at least one of web, a grid, or a mesh.

11. The method according to claim 1, wherein the total dose of ionizing radiation is between about 1 kGy and about 1,000 kGy.

12. The method according to claim 1, wherein the dose of ionizing radiation is between about 1 kGy and about 120 kGy.

13. The method according to claim 1, wherein the dose of ionizing radiation is between about 1 kGy and about 40 kGy.

14. The method according to claim 1, wherein the ionizing radiation is e-beam radiation.

15. The method according to claim 1, wherein the ionizing radiation is x-ray radiation.

16. The method according to claim 1, wherein the ionizing radiation is gamma radiation.

17. The method according to claim 7, wherein the conductive metallic layer contains aluminum.

18. The method according to claim 8, wherein the dose of ionizing radiation is between about 1 kGy and about 1000 kGy.

19. The method according to claim 8, wherein the dose of ionizing radiation is between about 1 kGy and about 120 kGy.

20. The method according to claim 8, wherein the dose of ionizing radiation is between about 1 kGy and about 40 kGy.

\* \* \* \* \*